(12) United States Patent
Hongou et al.

(10) Patent No.: US 8,409,101 B2
(45) Date of Patent: Apr. 2, 2013

(54) ULTRASONIC PROBE AND ULTRASONIC DIAGNOSTIC APPARATUS

(75) Inventors: Hironobu Hongou, Otawara (JP); Takatoshi Okumura, Yaita (JP); Kazuhito Nakata, Otawara (JP); Kenichi Unayama, Otawara (JP); Takeshi Fukasawa, Otawara (JP); Takayuki Shiina, Otawara (JP); Fumio Mochizuki, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 119 days.

(21) Appl. No.: 12/815,825

(22) Filed: Jun. 15, 2010

(65) Prior Publication Data
US 2010/0331702 A1  Dec. 30, 2010

(30) Foreign Application Priority Data
Jun. 24, 2009  (JP) .................................. 2009-150037

(51) Int. Cl.
*A61B 8/14* (2006.01)

(52) U.S. Cl. ......................................... 600/459; 600/437

(58) Field of Classification Search ........... 600/437–469
See application file for complete search history.

(56) References Cited

U.S. PATENT DOCUMENTS

| | | | | |
|---|---|---|---|---|
| 4,748,985 A * | 6/1988 | Nagasaki | ..................... | 600/445 |
| 5,560,362 A * | 10/1996 | Sliwa et al. | ..................... | 600/439 |
| 5,961,465 A * | 10/1999 | Kelly et al. | ..................... | 600/459 |
| 6,053,912 A * | 4/2000 | Panescu et al. | ................. | 606/40 |
| 6,436,130 B1 * | 8/2002 | Philips et al. | .................. | 607/105 |
| 7,052,463 B2 * | 5/2006 | Peszynski et al. | ............ | 600/459 |
| 7,918,799 B2 * | 4/2011 | Haveri | .......................... | 600/459 |
| 8,273,025 B2 * | 9/2012 | Shikata | ........................ | 600/437 |
| 2006/0100513 A1 * | 5/2006 | Hashimoto | ................... | 600/437 |
| 2007/0232923 A1 * | 10/2007 | Asuri | ............................ | 600/459 |
| 2008/0077017 A1 * | 3/2008 | Hyuga | .......................... | 600/459 |
| 2010/0163083 A1 * | 7/2010 | Suzuki et al. | ................. | 134/184 |
| 2011/0282211 A1 * | 11/2011 | Shikata | ........................ | 600/459 |

FOREIGN PATENT DOCUMENTS

| | | |
|---|---|---|
| CN | 101317772 A | 12/2008 |
| JP | 2007-275458 A | 10/2007 |
| WO | 2006/033281 A1 | 3/2006 |
| WO | 2009/035907 A2 | 3/2009 |

OTHER PUBLICATIONS

CN Office Action and English translation for corresponding CN Application No. 201010206033.3 mailed on Feb. 14, 2012.
CN Office Action with English Summary for CN Application No. 201010206033.3 mailed on Dec. 21, 2012.

* cited by examiner

*Primary Examiner* — Sanjay Cattungal
(74) *Attorney, Agent, or Firm* — Yoshida & Associates, LLC

(57) ABSTRACT

According to one embodiment, an ultrasonic probe includes a probe unit and cooling unit. The probe unit is obtained by arranging, in a housing, a transducer unit which transmits and receives ultrasonic waves with an object to be examined, an electronic circuit unit which is connected to the transducer unit and performs electrical signal processing, and a heat transfer member which is made of a material having a heat transfer coefficient higher than that of the electronic circuit unit, and transfers heat of the electronic circuit unit to a housing surface. The cooling unit is detachably mounted on the housing of the probe unit, and cools the heat transfer member by passing a coolant in a channel formed inside the cooling unit.

20 Claims, 6 Drawing Sheets

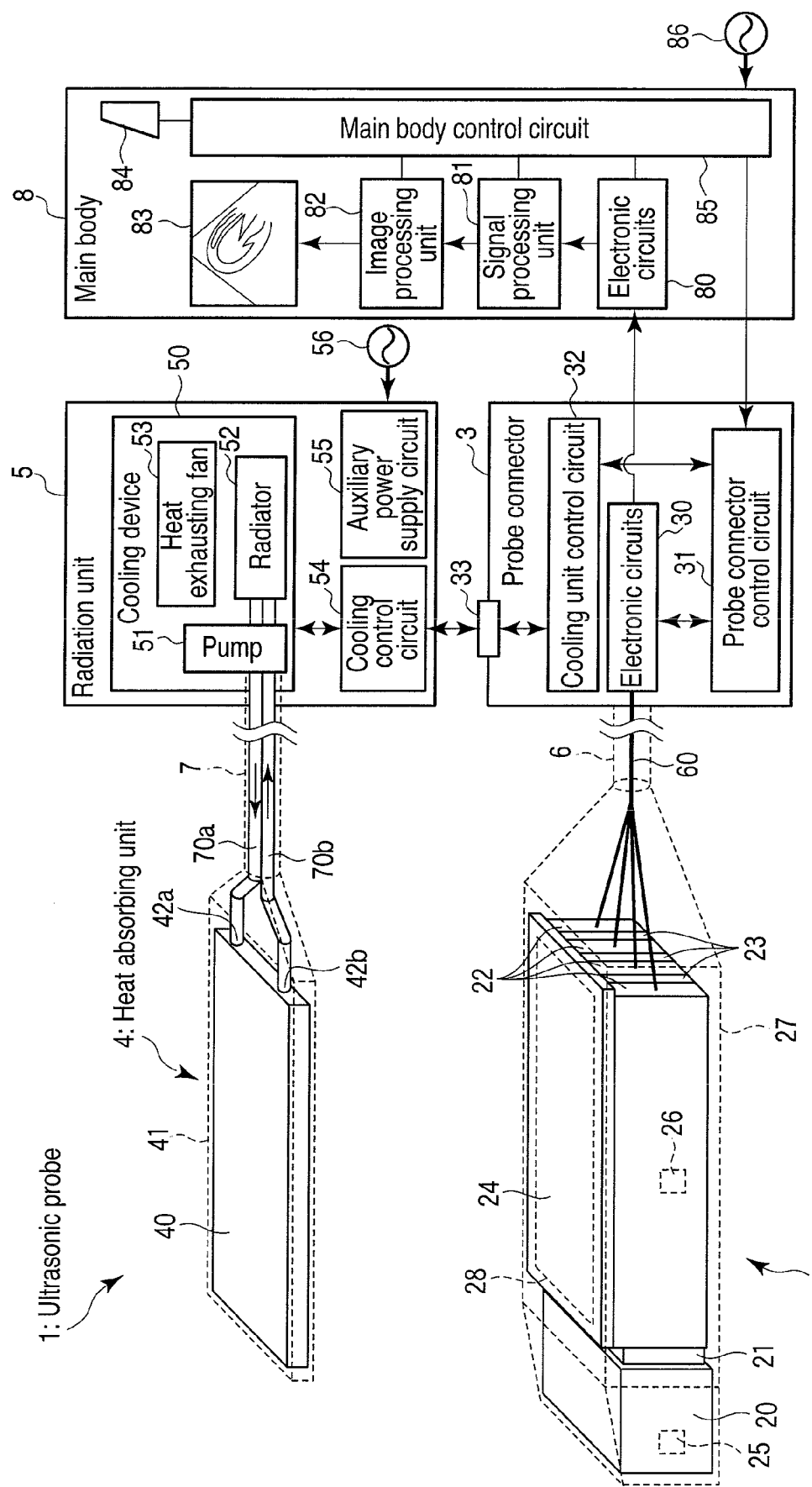
F I G. 3

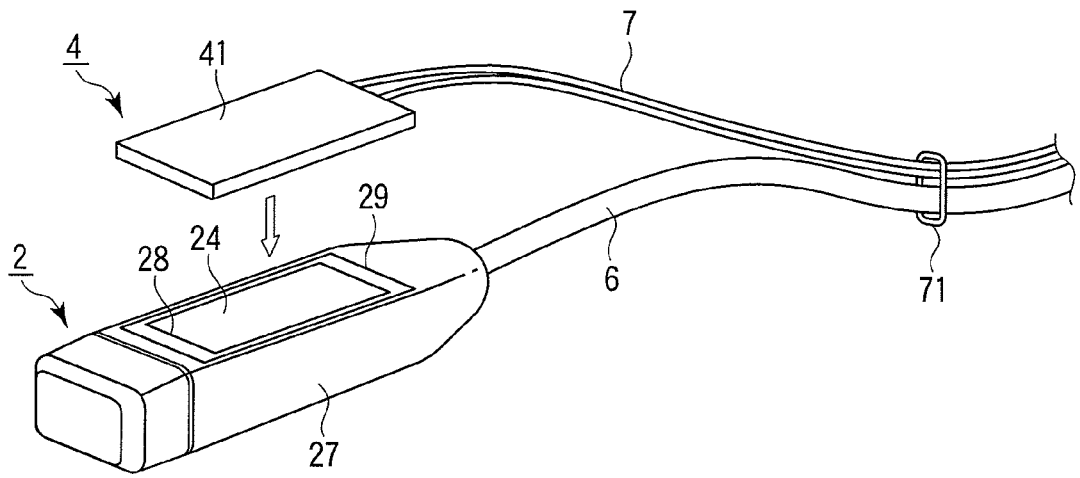
F I G. 4
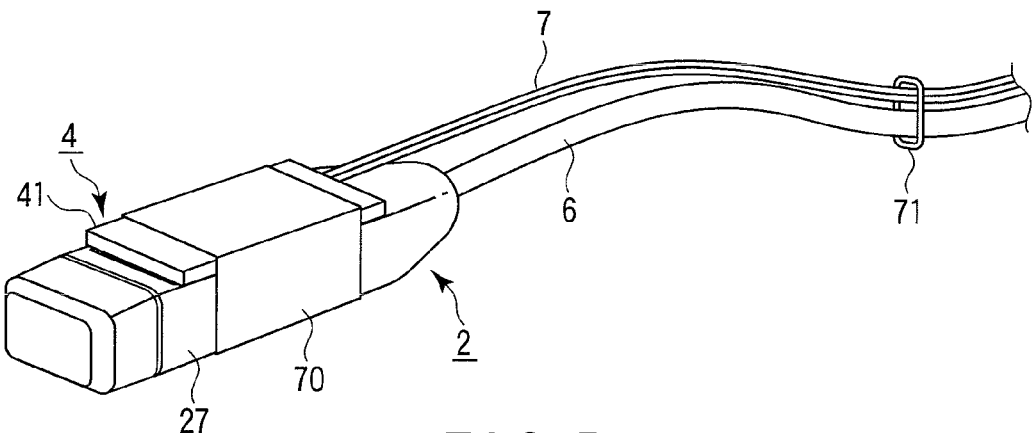
F I G. 5
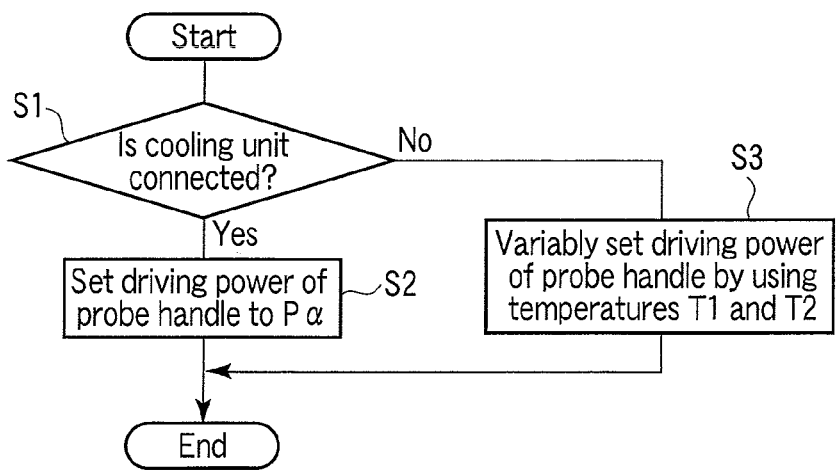
F I G. 6

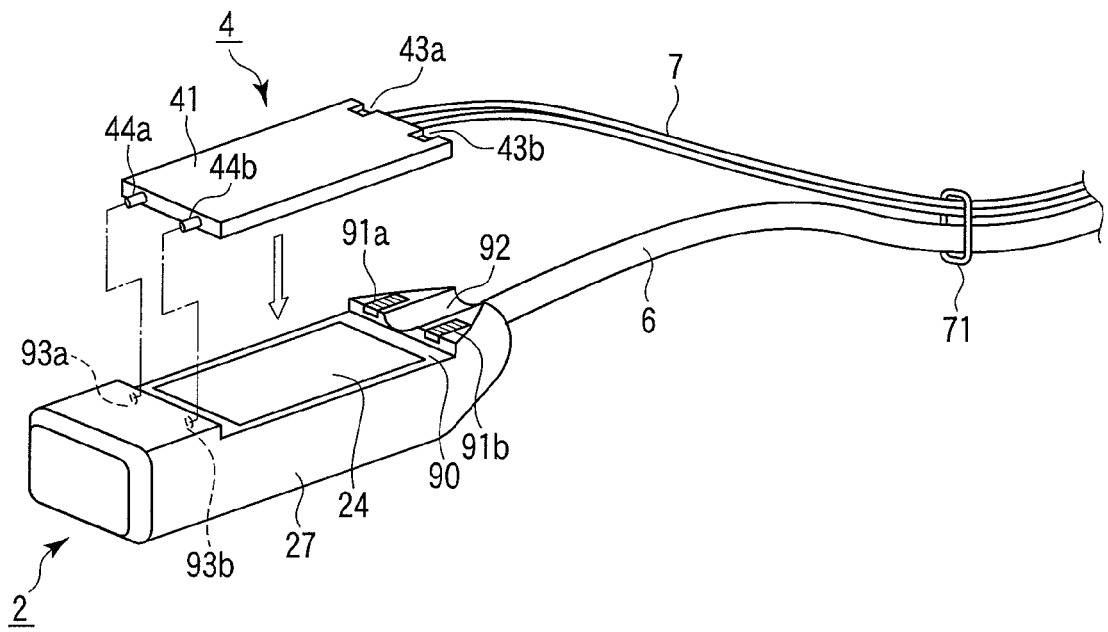
F I G. 7
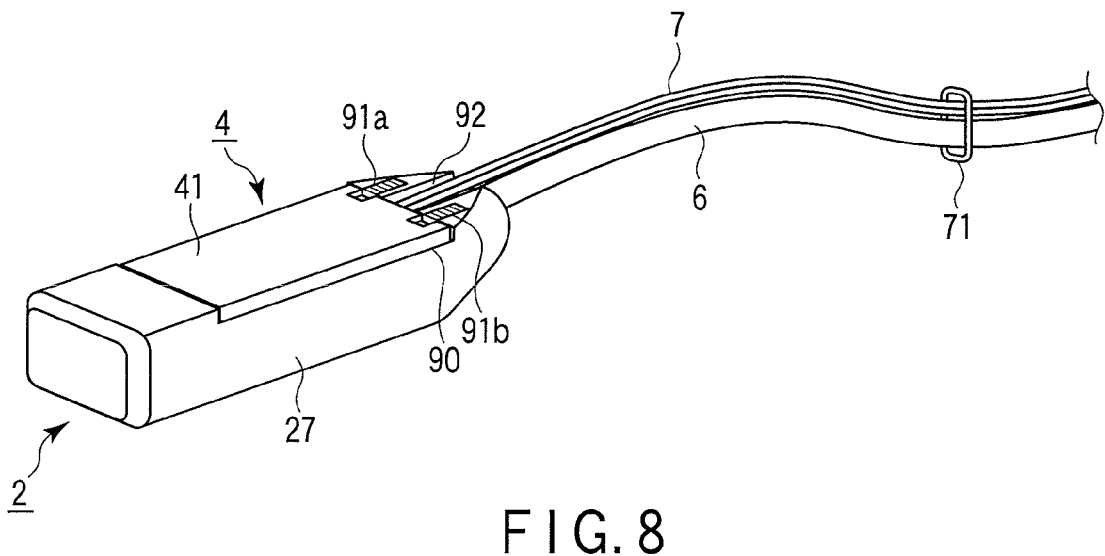
F I G. 8

ULTRASONIC PROBE AND ULTRASONIC DIAGNOSTIC APPARATUS

CROSS-REFERENCE TO RELATED APPLICATIONS

This application is based upon and claims the benefit of priority from Japanese Patent Application No. 2009-150037, filed Jun. 24, 2009; the entire contents of which are incorporated herein by reference.

FIELD

Embodiments described herein relate generally to an ultrasonic probe for scanning an ultrasonic beam on an object to be examined, and an ultrasonic diagnostic apparatus which displays an image of the interior of the object in real time based on a signal obtained by the ultrasonic probe by scanning the ultrasonic beam.

BACKGROUND

Recently, two-dimensional array transducers are beginning to be used in ultrasonic probes, so the number of transducers has increased to several thousands, and the size of each individual transducer has extremely decreased. Connecting an ultrasonic probe directly to an ultrasonic diagnostic apparatus of this type requires a large-diameter cable in which very many electronic lines can be inserted. The use of this large-diameter cable interferes with operations, and makes it difficult to efficiently transmit a driving waveform to a microtransducer, and transmit a high-quality ultrasonic echo received by a microtransducer. For an ultrasonic probe using two-dimensional array transducers, therefore, the efficiency of the driving of microtransducers and the efficiency of the amplification of an ultrasonic echo are increased by incorporating electronic circuits such as a transmitting circuit and receiving circuit in a probe handle. In addition, the number of signal lines input to an ultrasonic diagnostic apparatus is often reduced by performing partial receiving beam forming for every several transducers and adding the results.

FIG. 1 shows the arrangement of an ultrasonic diagnostic apparatus of this type. This ultrasonic diagnostic apparatus includes an ultrasonic probe 100 including a probe handle 110 and a probe connector 130 connected to the handle 110 via a probe cable 120, and an ultrasonic diagnostic apparatus main body 150 connected to the probe connector 130 via a main body probe connector 140.

The probe handle 110 includes transducers 111 arranged in the form of an array, pulsers 112 for generating an ultrasonic beam having a predetermined directionality by driving the transducers 111, preamplifiers 113 for performing processing such as low-noise amplification or buffering for satisfactorily transmitting very small ultrasonic echo signals received by the transducers 111, a sub-array beam former 114 for adding output signals from the preamplifiers 113 by giving a delay time to each group of a few channels, thereby reducing the number of output signal lines from the probe handle 110, and a control circuit 115 for controlling the individual components in the probe handle 110.

The probe connector 130 includes electronic circuits 131 for performing additional processing such as amplification, buffering, or band adjustment on ultrasonic echo signals as needed, and a probe connector control circuit 132 for generating a control signal to be transmitted to the control circuit 115 of the probe handle 110, based on a control signal transmitted from the ultrasonic diagnostic apparatus main body 150.

The ultrasonic diagnostic apparatus main body 150 includes main body preamplifiers 151 for amplifying the ultrasonic echo signals to which the delay is added for each group of a few channels in the probe handle 110, a reception delay addition circuit 152 for matching the timings of the amplified signals, a signal processing unit 153 for detecting the signals and extracting the envelope, an image processing unit 154 for transforming coordinates in accordance with the section of the object, a display unit 155 for displaying image data having the transformed coordinates, a main body control circuit 156 for controlling each unit, an operation panel 157 for accepting user's operations, a main body transmission delay circuit 158, and main body pulsers 159. The main body transmission delay circuit 158 and main body pulsers 159 operate a probe incorporating no electronic circuits when the probe is connected instead of the ultrasonic probe 100. This ultrasonic diagnostic apparatus can also detect and process the Doppler shift frequency of an ultrasonic beam resulting from the movement of blood cells generated when ultrasonic waves are exchanged with a blood flow in an object to be examined, and display blood flow velocity information as a Doppler image.

Since the ultrasonic wave transmitting and receiving processes are performed in the probe handle 110 as described above, electric power must be supplied to the built-in electronic circuits of the probe handle 110. However, to obtain, from an object to be examined, high-quality ultrasonic signals that can contribute to diagnosis, it is necessary to maintain a high transmitting/receiving performance by supplying considerable electric power. Consequently, the built-in electronic circuits generate heat and raise the temperature. This state interferes with operations, and may damage the object because the heat is conducted to the surface in contact with the object. Furthermore, the built-in electronic circuits themselves may break.

If the amount of power supplied to the probe handle 110 is reduced, however, the performance degrades to make it impossible to obtain necessary information, thereby interfering with diagnosis. Recently, therefore, a two-dimensional (2D) array probe including a cooling unit for cooing a probe handle by circulating a coolant is particularly beginning to be used.

FIG. 2 shows an example of the cooling unit using a coolant. This cooling unit includes a heat absorbing unit 160 in which a coolant channel is formed, a cooling device 162 connected to the channel of the heat absorbing unit 160 by cooling tubes 161a and 161b, and a cooling control circuit 163 for controlling the cooling device 162.

The cooling device 162 includes a pump for circulating the coolant, a radiator having a large number of radiation fins, and a cooling fan for supplying cooling air to the radiator. Under the control of the cooling control circuit 163, the cooling device 162 circulates the coolant by driving the built-in pump, and cools the coolant by rotating the cooling fan. The cooled coolant is supplied to the heat absorbing unit 160, and takes heat from circuits of a probe handle 110. This prevents the temperature rise of the circuits.

When attaching the cooling unit as described above, however, a very small forced cooling system is necessary because the volume of the probe handle is only about 100 cc. This complicates the structure of the ultrasonic probe, and probably makes it impossible to secure a sufficient durability. Also, it is difficult to obtain a sufficient cooling performance because the installation space of the cooling unit is limited.

Furthermore, if the cooling unit fails, it is difficult to repair the fault cooling unit, so an expensive ultrasonic probe must be discarded.

Under the circumstances, demands have arisen for an ultrasonic probe in which the structure of a probe handle is a simple structure similar to a natural air cooling structure, and a forced cooling unit can easily be replaced even if it fails.

BRIEF DESCRIPTION OF THE DRAWINGS

FIG. 3 is an exemplary view showing the arrangement of an ultrasonic diagnostic apparatus according to the first embodiment;

FIG. 4 is a perspective view showing the outer appearance before a probe handle and heat absorbing unit are assembled in the first embodiment;

FIG. 5 is a perspective view showing the outer appearance after the probe handle and heat absorbing unit are assembled in the first embodiment;

FIG. 6 is a flowchart showing the operation of a main body control circuit according to the first embodiment;

FIG. 7 is a perspective view showing the outer appearance before a probe handle and heat absorbing unit are assembled in the second embodiment;

FIG. 8 is a perspective view showing the outer appearance after the probe handle and heat absorbing unit are assembled in the second embodiment;

DETAILED DESCRIPTION

Figure 1:
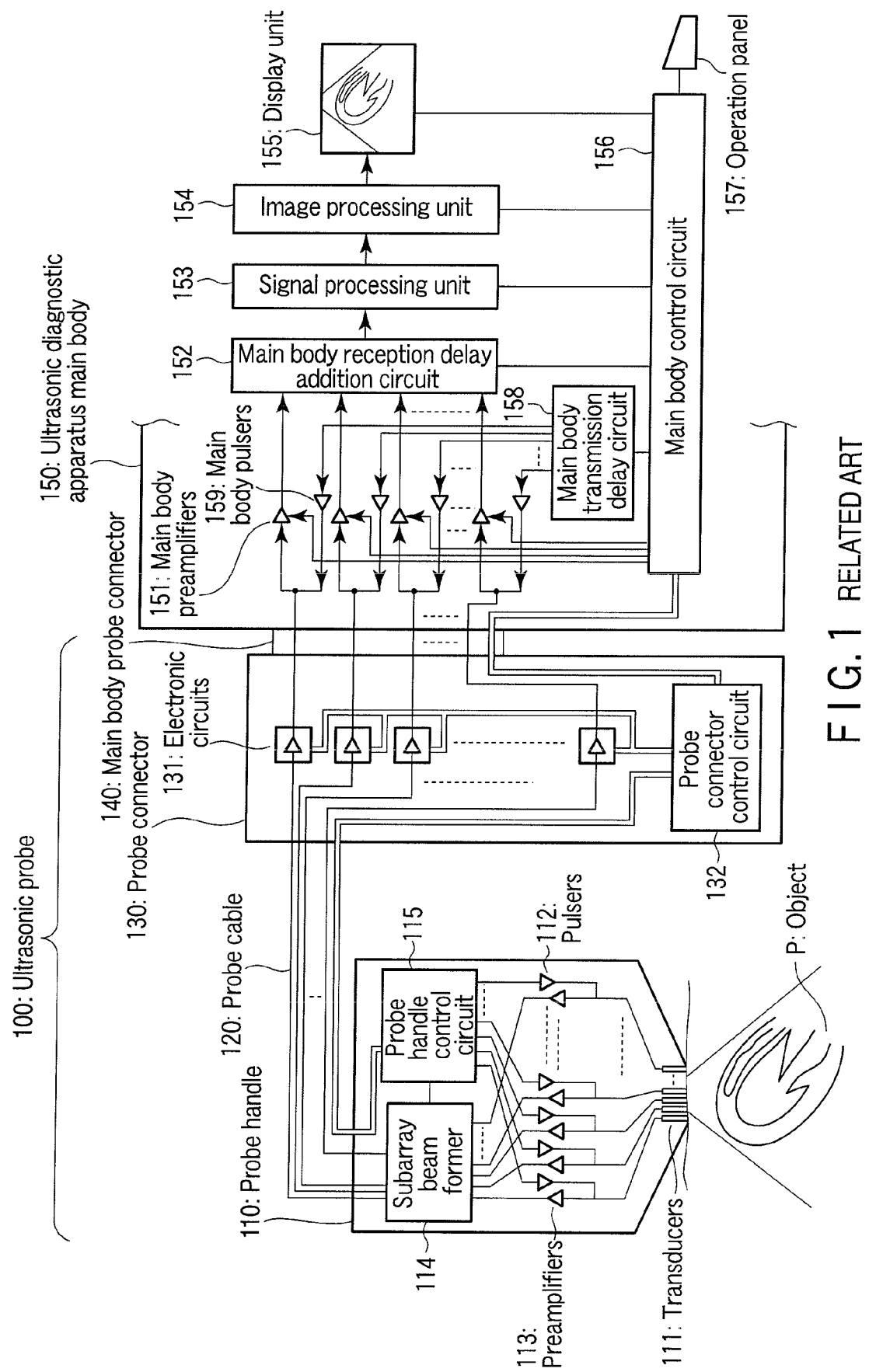
FIG. 1 is a view showing the arrangement of an ultrasonic diagnostic apparatus related to each embodiment.
Figure 2:
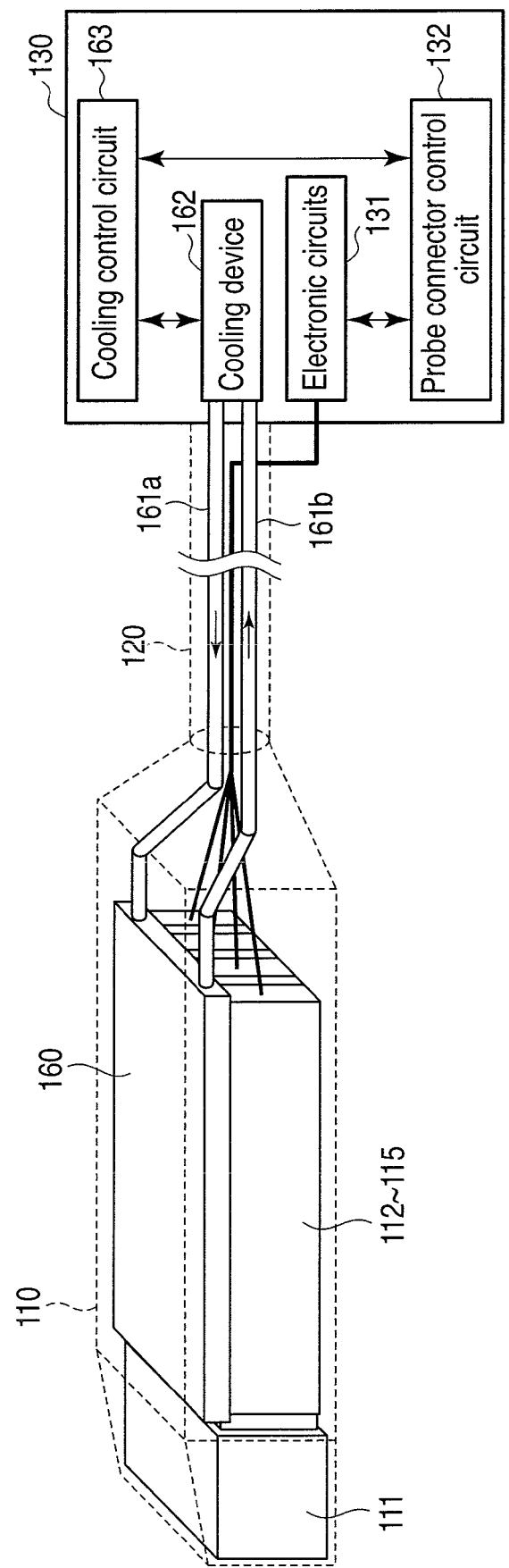
FIG. 2 is a view showing the arrangements of a probe handle and probe connector related to each embodiment.

In general, according to one embodiment, an ultrasonic probe includes a probe unit and cooling unit. The probe unit is obtained by arranging, in a housing, a transducer unit which transmit and receives ultrasonic waves with an object to be examined, an electronic circuit unit which is connected to the transducer unit and performs electrical signal processing, and a heat transfer member which is made of a material having a heat transfer coefficient higher than that of the electronic circuit unit, and transfers heat of the electronic circuit unit to a housing surface. The cooling unit is detachably mounted on the housing of the probe unit, and cools the heat transfer member by passing a coolant in a channel formed inside the cooling unit.

The first, second, and third embodiments will be explained below with reference to the accompanying drawings. Note that in the following explanation, the same reference numerals denote constituent components having almost the same functions and arrangements, and a repetitive explanation will be made only when necessary.

(First Embodiment)

FIG. 3 is an exemplary view showing the arrangement of an ultrasonic diagnostic apparatus according to the first embodiment. This ultrasonic diagnostic apparatus includes an ultrasonic probe 1 and main body 8. The ultrasonic probe 1 includes a probe handle 2 (probe unit) for transmitting and receiving ultrasonic waves, a probe connector 3 (connector unit) connected to the ultrasonic diagnostic apparatus main body, a heat absorbing unit 4 for absorbing heat generated by built-in electronic circuits of the probe handle 2, and a radiation unit 5 for radiating the heat absorbed by the heat absorbing unit 4. The probe handle 2 and probe connector 3 are connected via a flexible probe cable 6 (signal cable). The heat absorbing unit 4 and radiation unit 5 are connected via a flexible cooling cable 7. Note that the heat absorbing unit 4 and radiation unit 5 construct a cooling unit according to this embodiment.

The arrangement of each unit will be explained below.
[Probe Handle]

The probe handle 2 is obtained by arranging, in a housing 27, ultrasonic transducers 20 (a transducer unit), a connecting portion 21, electronic circuits 22 (an electronic circuit unit), heat spreaders 23, a heat sink 24, and temperature sensors 25 and 26.

The ultrasonic transducers 20 are obtained by arranging ultrasonic transducers into, e.g., an N×M array (N, M; integers). The ultrasonic transducers 20 transmit and receive ultrasonic waves with an object to be observed.

The electronic circuits 22 include pulsers, preamplifiers, subarray beam formers, and a probe handle control circuit (none of them is shown), and are connected to the ultrasonic transducers 20 via the connecting portion 21. The pulsers are connected to the ultrasonic transducers 20, and drive the ultrasonic transducers 20 in accordance with different timings generated by the probe handle control circuit, thereby generating an ultrasonic beam having a predetermined directionality. The ultrasonic beam generated from the ultrasonic transducers 20 is reflected by interfaces having different acoustic impedances, e.g., the boundaries of structures inside the object to be observed. The ultrasonic transducers 20 having received the reflected waves output weak ultrasonic echo signals. The preamplifiers perform processing such as low-noise amplification or buffering in order to satisfactorily transmit the weak ultrasonic echo signals output from the ultrasonic transducers 20. The subarray beam formers add the output signals from the above-described preamplifiers by giving a delay time to each group of several channels, thereby reducing the number of output signal lines from the probe handle 2. This reduces the number of signal lines 60 to be inserted into the probe cable 6. The probe handle control circuit controls the operations of the pulsers, preamplifiers, and subarray beam formers described above. The operating conditions such as bias electric currents of the preamplifiers can individually be set by control signals from this control circuit.

The heat spreaders 23 are formed in tight contact with individual electronic substrates of the electronic circuits 22 so as to be interposed between the electronic substrates. The heat spreaders 23 guide heat generated by the electronic circuits 22 in operation to the heat sink 24.

The heat sink 24 is a plate-like member having a size covering the electronic circuits 22 and heat spreaders 23, and guides the heat conducted from the heat spreaders 23 to the housing surface of the probe handle 2.

The heat spreaders 23 and heat sink 24 for guiding heat as described above have a structure mainly made of a material having a heat transfer coefficient higher than those of the electronic parts arranged in the housing 27 of the probe handle 2. Examples are a structure obtained by coating the surface of a main body made of SiC with a multilayered metal film of Ni/Ti/Pt/Au, and a structure obtained by plating the surface of a Cu member with Au for preventing oxidation. Note that the heat spreaders 23 and heat sink 24 construct a heat transfer member according to this embodiment.

The temperature sensor 25 is set for the ultrasonic transducers 20, and senses a temperature T1 near the ultrasonic transducers 20. The temperature sensor 26 is set in a predetermined position of the electronic circuits 22, and senses a temperature T2 of the electronic circuits 22. Note that the temperature sensors 25 and 26 are respectively positioned to be able to sense the temperatures of positions where the temperatures rise most easily in the ultrasonic transducers 20 and electronic circuits 22.

An opening 28 for exposing one surface of the heat sink 24 is formed in the surface of the housing 27 on the side where the heat sink 24 is installed.

[Probe Connector]

The probe connector 3 includes electronic circuits 30, a probe connector control circuit 31, a cooling unit control circuit 32 (detection unit), and a cooling unit control connector 33. The probe connector 3 is connected to a control circuit and power supply circuit of the main body 8 of the ultrasonic diagnostic apparatus by a connecting mechanism (not shown), and operates by receiving power supply from the main body 8.

The electronic circuits 30 performs, as needed, additional processing such as amplification, buffering, or band adjustment on ultrasonic echo signals transmitted from the probe handle 2 via the signal lines 60.

The cooling unit control circuit 32 controls power supply to the cooling unit, and notifies the radiation unit 5 of the temperature T1 sensed by the temperature sensor 25 and the temperature T2 sensed by the temperature sensor 26.

The cooling unit control connector 33 detachably connects the control circuit and power supply circuit of the probe connector 3 to those of the cooling unit.

The probe connector control circuit 31 controls the operation of the electronic circuits 30, and generates a control signal to be transmitted to the probe handle 2, based on a control signal transmitted from the main body 8. The control circuit 31 also has a function of detecting the connection state of the cooling unit with respect to the cooling unit control connector 33. Based on the detection result obtained by this function, the control circuit 31 notifies the main body 8 of the ultrasonic diagnostic apparatus of information indicating whether the cooling unit is connected, and the temperature T1 sensed by the temperature sensor 25 and the temperature T2 sensed by the temperature sensor 26. This notification is performed when the connection state of the cooling unit has changed, or when the temperature T1 or T2 has changed to exceed a predetermined value from the value of the last notification. It is also possible to periodically perform the notification every predetermined period.

[Heat Absorbing Unit]

The heat absorbing unit 4 includes a plate-like heat exchanger 40 made of a material having a high heat transfer coefficient, and a case-like housing 41 covering the heat exchanger 40.

A zigzagged coolant channel is formed inside the heat exchanger 40. The heat absorbing unit 4 has a supply hole 42a for supplying a coolant (supply coolant) to the channel, and a discharge hole 42b for discharging the coolant from the channel. The supply hole 42a and discharge hole 42b are respectively connected to a supply pipe 70a and discharge pipe 70b (supply/discharge pipes) made of a flexible material such as silicone rubber or soft vinyl chloride resin. The supply pipe 70a and discharge pipe 70b are inserted into the cooling cable 7. Note that the above-mentioned coolant is, e.g., a fluorine-based inert liquid that is thermally and chemically stable, and superior in electrical insulation properties and permeability.

The housing 41 has an opening (not shown) for exposing the heat exchanger 40, in the surface to be attached to the probe handle 2. This opening has almost the same width as that of the opening 28 in the housing 27 of the probe handle 2.

[Radiation Unit]

The radiation unit 5 includes a cooling device 50 including a pump 51 (coolant circulating unit), radiator 52, and heat exhausting fan 53, a cooling control circuit 54 (cooling control unit), and an auxiliary power supply circuit 55. Note that the radiator 52 and heat exhausting fan 53 construct a coolant cooling unit according to this embodiment.

The supply pipe 70a and discharge pipe 70b described above are connected to the pump 51 and radiator 52. The pump 51 supplies the coolant to the internal channel of the heat exchanger 40 via the supply pipe 70a. In addition, the pump 51 collects the coolant and sends it to the radiator 52 via the discharge pipe 70b. The heat exhausting fan 53 supplies cooling air to the radiator 52, and exhausts heat collected from the heat exchanger 40 by the coolant to the outside of the radiation unit 5 from an exhaust hole (not shown).

Based on the temperatures T1 and T2 notified from the probe connector 3, the cooling control circuit 54 adjusts the flow rate of the coolant by controlling the output of the pump 51, and adjusts the amount of air to be supplied to the radiator 52 by controlling the rotating speed of the heat exhausting fan 53. More specifically, if the temperatures T1 and T2 exceed a predetermined threshold value $T\alpha$ ($T\alpha < T1, T2$), the cooling control circuit 54 increases the output of the pump 51 and the rotating speed of the heat exhausting fan 53. If the temperatures T1 and T2 become lower than the threshold value $T\alpha$ ($T1, T2 < T\alpha$), the cooling control circuit 54 reduces the output of the pump 51 and the rotating speed of the heat exhausting fan 53. Note that the threshold value $T\alpha$ is set so as not to exceed the rated temperature of the ultrasonic transducers 20 or electronic circuits 22. By thus controlling the cooling device 50 based on the temperatures T1 and T2, it is possible to prevent the temperature rise of the probe handle 2, and obtain a high ultrasonic transmitting/receiving performance.

The auxiliary power supply circuit 55 monitors the voltage of the power supplied from the probe connector 3. If the voltage becomes lower than a necessary and sufficient value for the operation of the cooling unit, the auxiliary power supply circuit 55 is triggered to load operating power from an auxiliary power supply 56 such as a battery, and supplies the power to each unit of the radiation unit 5. Note that a switch connected to the auxiliary power supply 56 may also be formed on the housing of the radiation unit 5. In this case, the auxiliary power supply circuit 55 is triggered to switch the power supplies when the user manually operates the switch.

[Ultrasonic Diagnostic Apparatus Main Body]

The main body 8 of the ultrasonic diagnostic apparatus includes electronic circuits 80, a signal processing unit 81, an image processing unit 82, a display unit 83, an operation panel 84, and a main body control circuit 85 (control unit). Each unit of the main body 8 operates by loading operating power from a power supply 86.

The electronic circuits 80 include preamplifiers, pulsers, a reception delay addition circuit, a transmission delay addition circuit, and the like. The preamplifiers amplify ultrasonic echo signals having undergone the reception delay adding process performed for each group of several channels by the ultrasonic probe 1. The reception delay addition circuit matches the timings of the ultrasonic echo signals amplified by the preamplifiers, and outputs the signals to the signal processing unit 81.

The signal processing unit 81 detects the ultrasonic signals output from the electronic circuits 80, and extracts the envelope. The image processing unit 82 performs coordinate conversion, tone processing, or the like on the ultrasonic signals from which the envelope is extracted by the signal processing unit 81, in accordance with the section of an object to be observed, and outputs the signals to the display unit 83. Based on the data output from the image processing unit 82, the display unit 83 displays the diagnostic image of the object. The operation panel 84 accepts various user's operations.

The main body control circuit 85 controls each unit of the main body 8, and outputs control signals concerning the driving of the probe handle 2 to the probe connector control circuit 31.

[Shapes of Probe Handle and Heat Absorbing Unit]

The shapes of the probe handle 2 and heat absorbing unit 4 will be explained below with reference to FIGS. 4 and 5. FIG. 4 is a perspective view showing the outer appearances of the probe handle 2 and heat absorbing unit 4 before they are assembled. FIG. 5 is a perspective view showing the outer appearances of the probe handle 2 and heat absorbing unit 4 after they are assembled.

As shown in FIG. 4, the housing of the probe handle 2 has a recess 29 (guiding portion) indicating the attaching position of the heat absorbing unit 4. The opening 28 of the housing 27 is positioned on the bottom surface of the recess 29, and the upper surface of the heat sink 24 is exposed from the opening 28. Since the exposed surface of the heat sink 24 probably touches the skin of a user or patient, it is desirable to form an insulating protective film. However, if the internal structure of the probe handle 2 can insulate the heat sink 24, priority may be given to the thermal conductivity to the heat absorbing unit 4 without forming any protective film.

When attaching the heat absorbing unit 4 to the probe handle 2, the housing 41 of the heat absorbing unit 4 is positioned on and pressed against the above-mentioned recess 29. The inclined portions of the recess 29 abut against the housing 41 of the heat absorbing unit 4, and guide the heat absorbing unit 4 to the position where the heat absorbing unit 4 is in contact with the portion to which heat is transferred by the heat sink 24. In this state, the probe handle 2 and heat absorbing unit 4 are fixed by winding a fixing belt 70 (fixing portion) as shown in FIG. 5. Consequently, the exposed surface of the heat sink 24 is brought into tight contact with the heat exchanger 40 exposed from the opening surface of the housing 41 of the heat absorbing unit 4. Even when a force is applied to the heat absorbing unit 4 in a direction to slide the heat absorbing unit 4 on the housing 27 of the probe handle 2, the heat absorbing unit 4 is not easily removed from the fixing position because the side surfaces of the housing 41 of the heat absorbing unit 4 are pushed against the inclined portions of the recess 29.

The fixing belt 70 is a member suited to fixing the heat absorbing unit 4 to the probe unit 2. Examples are a member obtained by attaching a hook-and-loop fastener to a belt-like elastic member, and a ring-like elastic member. Also, when using an insulating member having a size completely covering the housing 41 of the heat absorbing unit 4 attached to the probe handle 2, the probability that the exposed surface of the heat sink 24 touches a human body can be eliminated without forming any insulating protective film on the exposed surface of the heat sink 24. This can further improve the cooling performance of the cooling unit. Furthermore, when coating the exposed surface of the heat sink 24 with a thermal conductor such as silicone grease, it is possible to prevent an air layer from being formed between the heat sink 24 and heat exchanger 40, and increase the thermal conductivity from the heat sink 24 to the thermal exchanger 40.

Note that the probe cable 6 and cooling cable 7 are bound by a cable binder 71 so as not to interfere with the diagnosing operation by unbound cables.

When the cooling unit is thus attached to the probe handle 2 and probe connector 3, the pump 51 and heat exhausting fan 53 of the cooling device 50 are driven based on the sensed temperatures T1 and T2 of the temperature sensors 25 and 26 notified from the probe connector 3 as described previously. In this state, the coolant passing through the internal channel of the heat exchanger 40 cools the heat sink 24. The radiator 52 and heat exhausting fan 53 cool the coolant heated by the heat exchanger 40.

[Operation of Main Body Control Circuit]

The driving of the ultrasonic probe 1 by the main body control circuit 85 will be explained below.

When the user enters an instruction to start image sensing by operating the operation panel 84, the main body control circuit 85 executes the process of setting the driving power of the ultrasonic probe 1. FIG. 6 shows a flowchart of this process.

Immediately after the process is started, the main body control circuit 85 first determines whether the cooling unit is connected to the cooling unit control connector 33 (step S1). This processing is performed based on the information that is notified from the probe connector control circuit 31 as described previously, and indicates whether the cooling unit is connected.

If the probe connector control circuit 31 notifies the main body control circuit 85 of information indicating that the cooling unit is connected, the main body control circuit 85 determines that the cooling unit is connected (Yes in step S1). In this case, the main body control circuit 85 sets the driving power of the probe handle 2 to a prescribed value Pα (step S2). The prescribed value Pα is, e.g., electric power required to drive the probe handle 2 so as to obtain a highest-quality ultrasonic echo signal.

On the other hand, if the probe connector control circuit 31 notifies the main body control circuit 85 of information indicating that no cooling unit is connected, the main body control circuit 85 determines that no cooling unit is connected (No in step S1). In this case, the main body control circuit 85 variably sets the driving power of the probe handle 2 by using the temperatures T1 and T2 so as not to exceed the prescribed value Pα (step S3). For example, when the temperatures T1 and T2 are lower than the threshold value Tα, the main body control circuit 85 sets the driving power of the probe handle 2 to the prescribed value Pα. When the temperatures T1 and T2 are higher than the threshold value Tα, the main body control circuit 85 decreases the driving power of the probe handle 2 in proportion to one of the temperatures T1 and T2.

After setting the driving power as described above, the main body control circuit 85 terminates the process of this flowchart. After that, the main body control circuit 85 notifies the probe connector control circuit 31 of a control signal for driving the probe handle 2 by the driving force set by the processing in step S2 or S3. The probe connector control circuit 31 drives the probe handle 2 based on the control signal notified from the main body control circuit 85.

Note that the process shown in the flowchart of FIG. 6 is periodically executed even after the driving of the probe handle 2 is started, and the driving power of the probe handle 2 is set in accordance with the temperatures T1 and T2 sensed on each occasion. The period need only be set at a value by which even when the temperatures T1 and T2 abruptly rise, the probe handle 2 can be driven such that the temperature T1 does not exceed the rated temperature of the ultrasonic transducers 20, and the temperature T2 does not exceed the rated temperature of the electronic circuits 22.

The arrangement described above can achieve the following effects.

In the ultrasonic probe 1 according to this embodiment, the cooling unit is detachable from the probe handle 2 and probe connector 3. Even when the cooling unit fails, therefore, the cooling unit need only be repaired or replaced without discarding the ultrasonic probe 1.

Since the heat absorbing unit 4 of the cooling unit is independent of the probe handle 2, a simple structure similar to a natural air cooling structure can be used as the structure of the probe handle 2. This makes it possible to well ensure the durability of the structure of the probe handle 2.

Also, since the heat absorbing unit 4 need not be installed in the internal limited space of the probe handle 2, the large-sized heat absorbing unit 4 having a sufficient cooling performance can be used. Therefore, it is possible to drive the probe handle 2 by using high electric power that generates a large amount of heat, and obtain high-quality ultrasonic echo signals.

Furthermore, the driving power of the probe handle 2 is automatically adjusted in accordance with the connection state of the cooling unit with respect to the main body 8. Therefore, the user need not perform any cumbersome operation of, e.g., setting the driving power by checking the connection state of the cooling unit. In addition, even if the user forgets to connect the cooling unit to the probe connector 3 or a connection error occurs, the driving power is set such that the temperatures T1 and T2 do not exceed the rated temperatures of the ultrasonic transducers 20 and electronic circuits 22, respectively. Accordingly, the probe handle 2 can be protected against overheating.

(Second Embodiment)

The second embodiment will be explained below with reference to the accompanying drawings.

An ultrasonic probe according to this embodiment differs from the first embodiment in that a recess 29 is formed such that a housing 27 of a probe handle 2 and the upper surface of a heat absorbing unit 4 form an almost flat surface when attaching the heat absorbing unit 4 to the probe handle 2, and the probe handle 2 and heat absorbing unit 4 have a fixing mechanism. The circuit configuration and the like of an ultrasonic probe 1 are the same as those of the first embodiment, so a repetitive explanation will be omitted by denoting the same components by the same reference numerals.

FIG. 7 is a perspective view showing the outer appearances of the probe handle 2 and heat absorbing unit 4 according to this embodiment.

In this embodiment, a recess 90 is formed to have a depth that is almost the same as the thickness of the heat absorbing unit 4. A pair of stoppers 91a and 91b and a guide groove 92 are formed in the inner wall of the recess 90 on the side connected to a probe cable 6. A pair of fixing holes 93a and 93b are formed in the inner wall of the distal end of the probe handle 2.

The stoppers 91a and 91b are slide-type stoppers in which long projecting members are fitted in grooves formed in the housing of the probe handle 2, and slidably held in the direction to a position where the heat absorbing unit 4 is attached. The guide groove 92 is a circular groove formed from the side wall of the recess 90 to one end of the side connected to the probe cable 6, and having a curvature larger than that of a cooling cable 7.

A pair of grooves 43a and 43b are formed in the side wall of a housing 41 of the heat absorbing unit 4 on the side connected to the cooling cable 7. A pair of fixing pins 44a and 44b are formed on the side wall opposite to the former side wall.

The grooves 43a and 43b are respectively formed in positions corresponding to the stoppers 91a and 91b, and have shapes to be fitted on the projecting members of the stoppers 91a and 91b. The fixing pins 44a and 44b are respectively formed in positions corresponding to the fixing holes 93a and 93b, and have shapes to be fitted in the fixing holes 93a and 93b.

Note that the stoppers 91a and 91b, fixing holes 93a and 93b, grooves 43a and 43b, and fixing pins 44a and 44b construct the fixing mechanism according to this embodiment.

When attaching the heat absorbing unit 4 having the shape as described above to the probe handle 2, the fixing pins 44a and 44b are respectively inserted into the fixing holes 93a and 93b, thereby bringing the bottom surface (having an opening) in tight contact with the exposed surface of a heat sink 24 of the probe handle 2. The projecting members of the stoppers 91a and 91b are slid and fitted in the grooves 43a and 43b. In the state, the cooling cable 7 is positioned in the guide groove 92. Therefore, the cooling cable 7 does not interfere with the attachment of the heat absorbing unit 4.

When the heat absorbing unit 4 is thus attached to the probe handle 2, as shown in FIG. 8, the upper surface of the housing 27 of the probe handle 2 and the housing 41 of the heat absorbing unit 4 form an almost flat surface. In this state, the side walls of the recess 90 regulate the movement of the heat absorbing unit 4 in the longitudinal direction of the probe handle 2, and the fixing pins 44a and 44b, fixing holes 93a and 93b, and stoppers 91a and 91b regulate the movement of the heat absorbing unit 4 in the lateral direction of the probe handle 2 and the direction of the exposed surface of the heat sink 24.

The arrangement described above can achieve the following effects.

The ultrasonic probe 1 according to this embodiment includes the means for fixing the heat absorbing unit 4 to the probe handle 2. This obviates the need to prepare an additional fixing member unlike in the first embodiment, and facilitates attaching the cooling unit. This also saves the user the trouble of managing an additional fixing member such as the one used in the first embodiment.

Furthermore, when the heat absorbing unit 4 is attached, the housing 41 of the heat absorbing unit 4 does not protrude from the housing 27 of the probe handle 2. Even when the heat absorbing unit 4 is attached, therefore, it is possible to maintain the same operability of the probe handle 2 as that when the heat absorbing unit 4 is not attached.

In addition, this embodiment of course achieves the same effects as those of the first embodiment.

(Third Embodiment)

The third embodiment will be explained below with reference to the accompanying drawings.

An ultrasonic probe 1 according to this embodiment differs from the second embodiment in that a probe handle 2 includes a cover 94 for covering a position where a heat absorbing unit 4 is to be attached. The circuit configuration and the like of the ultrasonic probe 1 are the same as those of each embodiment described above, so a repetitive explanation will be omitted by denoting the same components by the same reference numerals.

Figure 9:
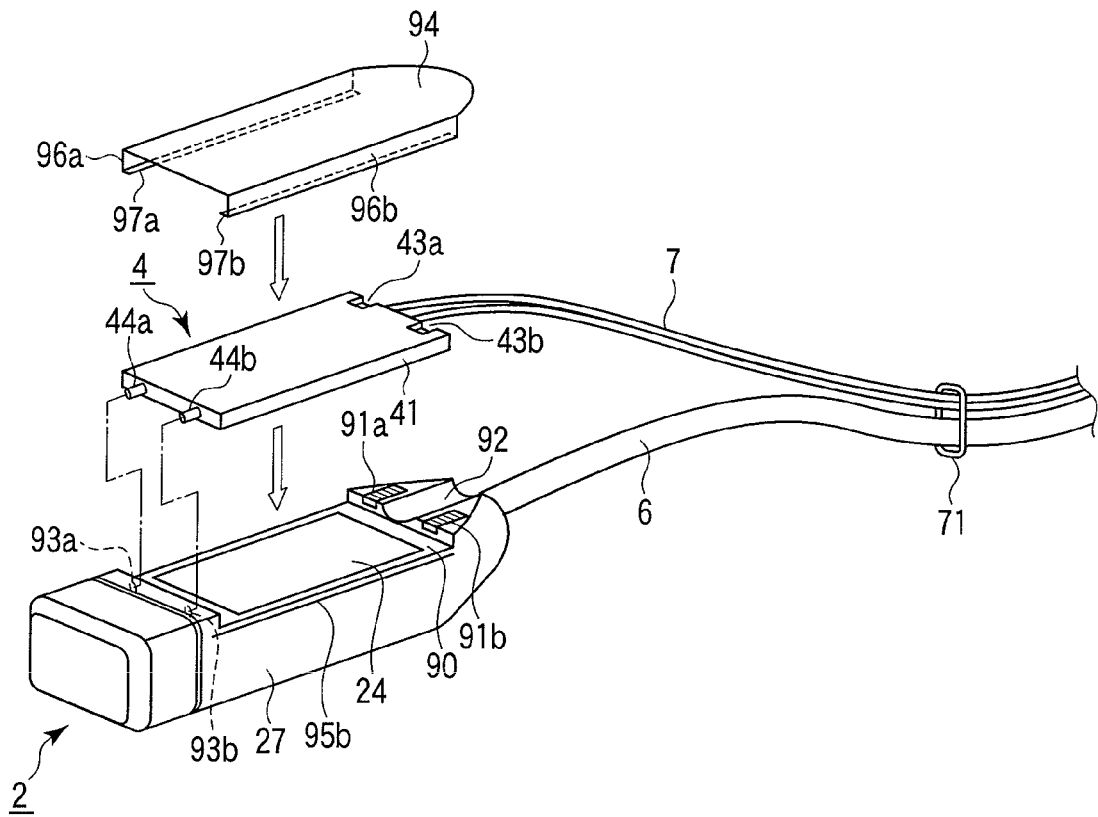
FIG. 9 is a perspective view showing the outer appearance before a probe handle and heat absorbing unit are assembled in the third embodiment.

FIG. 9 is a perspective view showing the outer appearances of the probe handle 2, heat absorbing unit 4, and cover 94.

The shape of the probe handle 2 is almost the same as that of the second embodiment except that a pair of grooves 95a and 95b (FIG. 9 shows only the groove 95b) are formed in the two side surfaces in the lateral direction of a housing 27, along the bottom surface of a recess 90.

The cover 94 is a plate-like member whose width in the lateral direction is almost the same as that of the probe handle 2, and the two end portions of this plate-like member along the longitudinal direction are bent inward. Guide portions 97a and 97b as the distal end portions of bent portions 96a and 96b are respectively fitted in the grooves 95a and 95b of the probe handle 2. Note that the cover 94 is made of an insulating material having a low thermal conductivity, e.g., plastic.

When attaching the cover 94, the heat absorbing unit 4 is first attached to the probe handle 2 as shown in FIG. 8 described previously. Then, the cover 94 is pushed from the side on which the heat absorbing unit 4 is attached. Consequently, the guide portions 97a and 97b are respectively fitted in the grooves 95a and 95b, and the cover 94 is fixed to the housing 27 of the probe handle 2.

Figure 10:
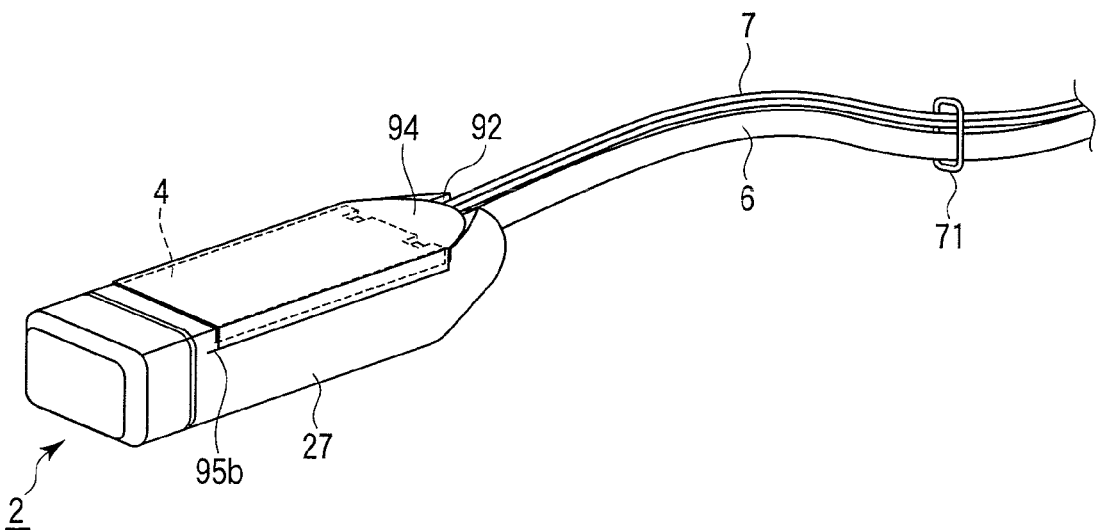
FIG. 10 is a perspective view showing the outer appearance after the probe handle and heat absorbing unit are assembled in the third embodiment.

When the heat absorbing unit 4 and cover 94 are thus attached to the probe handle 2, as shown in FIG. 10, the upper surface of the housing 27 of the probe handle 2 and the upper surface of the cover 94 form an almost flat surface, and the cover 94 completely covers the heat absorbing unit 4 attached to the probe handle 2. Note that a method of attaching the cover 94 to the housing 27 is not limited to the method using the guide portions 97a and 97b and grooves 95a and 95b, and can also be another method.

The arrangement described above can achieve the following effects.

In the ultrasonic probe 1 according to this embodiment, even when the heat absorbing unit 4 is attached to the probe handle 2, the heat absorbing unit 4 is not exposed because the cover 94 covers the whole attaching portion. Therefore, the cooling unit does not interfere with the operation of the probe handle 2.

Also, when the cover 94 is attached to the probe handle 2 regardless of whether to attach the heat absorbing unit 4, the portion to which the heat absorbing unit 4 is to be attached does not touch the skin of an operator or patient. Accordingly, the exposed surface of a heat sink 24 heated to a high temperature or the heat absorbing unit 4 does not burn an operator or patient by touching him or her.

In addition, this embodiment of course achieves the same effects as those of the embodiments described above.

(Modifications)

Various modifications can be made from the arrangements disclosed in the above-mentioned embodiments. Practical modifications are as follows.

(1) That is, in each embodiment described above, the control circuits of the probe connector 3 and radiation unit 5 are connected via the cooling unit control connector 33, and the cooling control circuit 54 controls the cooling device 50 based on the temperatures T1 and T2 notified from the probe connector 3. However, the control circuits of the radiation unit 5 and probe connector 3 may also be unconnected independent control systems. In this case, an operation unit including switches and the like is formed on, e.g., the housing of the radiation unit 5, and the user manually inputs control information to the cooling device 50. It is also possible to always operate the pump 51 and heat exhausting fan 53 of the cooling device 50 under predetermined conditions.

(2) In each embodiment described above, the cooling unit operating power is supplied from the probe connector 3 via the cooling unit control connector 33, and, if the voltage of this power supply drops, the auxiliary power supply circuit 55 loads power from the auxiliary power supply 56. However, it is also possible to supply no operating power from the probe connector 3 to the radiation unit 5, and supply power to the radiation unit 5 from a power supply system entirely independent of the probe connector 3 and the main body 8 of the ultrasonic diagnostic apparatus.

Increasing the independence of the radiation unit 5 and probe connector 3 as described in modifications (1) and (2) obviates the need to form the cooling unit control connector 33 and cooling unit control circuit 32 in the probe connector 3, and simplifies the structure of the ultrasonic probe 1. Also, when it is no longer necessary to supply power from the probe connector 3 to the cooling unit, a large part of the power supplied from the main power supply 34 can be used to drive the probe handle 2. This stabilizes the ultrasonic transmitting/receiving performance.

(3) When it is desirable to acquire images superior in spatial resolution and temporal resolution, higher electric power must be supplied to the probe handle 2, and this increases the amount of heat generated by the electronic circuits 22. Since this makes the cooling performance necessary to improve, the cooling unit must be enlarged, and the size and weight of the unit pose problems. If these problems arise, it is only necessary to appropriately use an auxiliary tool such as a support arm for supporting the probe handle 2.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic probe comprising:
   a probe unit obtained by arranging, in a housing, a transducer unit which transmits and receives ultrasonic waves with an object to be examined, an electronic circuit unit which is connected to the transducer unit and performs electrical signal processing, and a heat transfer member which is made of a material having a heat transfer coefficient higher than that of the electronic circuit unit, and transfers heat of the electronic circuit unit to a housing surface;
   a cooling unit which is detachably mounted on the housing of the probe unit, and cools the heat transfer member by passing a coolant in a channel formed inside the cooling unit; and
   a fixing member located on the housing and the cooling unit having a predetermined number of elements for engaging the cooling unit to the housing at a predetermine location, at least one of the elements being movable for locking the cooling unit on the housing.

2. The probe according to claim 1, wherein the heat transfer member comprises:
   a heat sink formed to expose one surface to the housing surface; and
   heat spreaders which are formed between electronic circuits constructing the electronic circuit unit, and transfer heat of the electronic circuits to the heat sink.

3. The probe according to claim 1, wherein the cooling unit comprises:
   a heat absorbing unit which is attached to the housing of the probe unit; and
   a radiation unit which is connected to the heat absorbing unit by coolant supply/discharge pipes, and cools the coolant heated by the heat absorbing unit.

4. The probe according to claim 3, wherein the probe unit further comprises a guiding portion which guides the heat absorbing unit to a position where the heat absorbing unit abuts against a portion on the housing surface to which heat is transferred by the heat transfer member.

5. The probe according to claim 3, wherein the probe unit further comprises a fixing portion which fixes the heat absorbing unit to the housing by bringing the heat absorbing unit in tight contact with a position to which heat is transferred by the heat transfer member.

6. The probe according to claim 3, wherein the probe unit further comprises a detachable cover which covers the heat absorbing unit attached to the housing of the probe unit.

7. The probe according to claim 3, wherein the radiation unit comprises:
a coolant circulating unit which circulates the coolant between the heat absorbing unit and the coolant circulating unit via the supply/discharge pipes; and
a coolant cooling unit which cools the coolant circulated by the coolant circulating unit.

8. The probe according to claim 7, which further comprises a connector unit which is connected to the probe unit via a communication cable, and transmits and receives signals with an ultrasonic diagnostic apparatus main body, and
in which the coolant circulating unit and the coolant cooling unit operate by receiving power from a power supply different from a power supply which supplies power to the connector unit and the ultrasonic diagnostic apparatus main body.

9. The probe according to claim 7, further comprising:
a temperature sensor which senses a temperature of the probe unit; and
a cooling control unit which controls the coolant circulating unit and the coolant cooling unit based on the temperature sensed by the temperature sensor.

10. An ultrasonic probe comprising:
a transducer unit which transmits and receives ultrasonic waves with an object to be examined;
an electronic circuit unit which is connected to the transducer unit and performs electrical signal processing;
a heat transfer member which is made of a material having a heat transfer coefficient higher than that of the electronic circuit unit, and transfers heat of the electronic circuit unit to a housing surface; and
a fixing portion which fixes, to a housing, a heat absorbing unit which cools the heat transfer member by circulating a coolant, by bringing the heat absorbing unit in tight contact with a portion to which heat is transferred by the heat transfer member, wherein the fixing portion having a predetermined number of elements for detachably engaging the heat absorbing unit to the housing at a predetermine location, at least one of the elements being movable for locking the heat absorbing unit on the housing.

11. The probe according to claim 10, further comprising a guide portion which guides the heat absorbing unit to a position where the heat absorbing unit abuts against a portion on the housing surface to which heat is transferred by the heat transfer member.

12. The probe according to claim 10, further comprising a detachable cover which covers the heat absorbing unit fixed to the housing by the fixing portion.

13. An ultrasonic diagnostic apparatus comprising:
a probe unit obtained by arranging, in a housing, a transducer unit which transmits and receives ultrasonic waves with an object to be examined, an electronic circuit unit which is connected to the transducer unit and performs electrical signal processing, and a heat transfer member which is made of a material having a heat transfer coefficient higher than that of the electronic circuit unit, and transfers heat of the electronic circuit unit to a housing surface;
a cooling unit which is detachably mounted on the housing of the probe unit, and cools the heat transfer member by passing a coolant in a channel formed inside the cooling unit;
a fixing member located on the housing and the cooling unit having a predetermined number of elements for engaging the cooling unit to the housing at a predetermine location, at least one of the elements being movable for locking the cooling unit on the housing;
a temperature sensor which senses a temperature of the probe unit;
a detection unit which detects a connection state of the cooling unit with respect to the probe unit; and
a control unit which operates the probe unit by prescribed power when the detection unit detects connection of the cooling unit, and operates the probe unit by power corresponding to the temperature sensed by the temperature sensor when the detection unit does not detect connection of the cooling unit.

14. The apparatus according to claim 13, wherein the heat transfer member comprises:
a heat sink formed to expose one surface to the housing surface; and
heat spreaders which are formed between electronic circuits constructing the electronic circuit unit, and transfer heat of the electronic circuits to the heat sink.

15. The apparatus according to claim 13, wherein the cooling unit comprises:
a heat absorbing unit which is attached to the housing of the probe unit; and
a radiation unit which is connected to the heat absorbing unit by coolant supply/discharge pipes, and cools the coolant heated by the heat absorbing unit.

16. The apparatus according to claim 15, wherein the probe unit further comprises a guide portion which guides the heat absorbing unit to a position where the heat absorbing unit abuts against a portion on the housing surface to which heat is transferred by the heat transfer member.

17. The apparatus according to claim 15, wherein the probe unit further comprises a fixing portion which fixes the heat absorbing unit to the housing by bringing the heat absorbing unit in tight contact with a position to which heat is transferred by the heat transfer member.

18. The apparatus according to claim 15, wherein the probe unit further comprises a detachable cover which covers the heat absorbing unit attached to the housing of the probe unit.

19. The apparatus according to claim 15, wherein the radiation unit comprises:
a coolant circulating unit which circulates the coolant between the heat absorbing unit and the coolant circulating unit via the supply/discharge pipes; and
a coolant cooling unit which cools the coolant circulated by the coolant circulating unit.

20. The apparatus according to claim 19, which further comprises a connector unit which is connected to the probe unit via a communication cable, and transmits and receives signals with an ultrasonic diagnostic apparatus main body, and
in which the coolant circulating unit and the coolant cooling unit operate by receiving power from a power supply different from a power supply which supplies power to the connector unit and the ultrasonic diagnostic apparatus main body.

* * * * *